(12) United States Patent
Baker et al.

(10) Patent No.: US 9,861,801 B2
(45) Date of Patent: Jan. 9, 2018

(54) DRUG DELIVERY DEVICE

(71) Applicant: Kimberly-Clark Worldwide, Inc., Neenah, WI (US)

(72) Inventors: Andrew Baker, Norcross, GA (US); Russell F. Ross, Atlanta, GA (US); Luke Hagan, Seattle, WA (US)

(73) Assignee: KIMBERLY-CLARK WORLDWIDE, INC., Neenah, WI (US)

(*) Notice: Subject to any disclaimer, the term of this patent is extended or adjusted under 35 U.S.C. 154(b) by 89 days.

(21) Appl. No.: 14/762,534

(22) PCT Filed: Feb. 28, 2014

(86) PCT No.: PCT/IB2014/059344
§ 371 (c)(1),
(2) Date: Jul. 22, 2015

(87) PCT Pub. No.: WO2014/132239
PCT Pub. Date: Sep. 4, 2014

(65) Prior Publication Data
US 2015/0360018 A1 Dec. 17, 2015

Related U.S. Application Data

(60) Provisional application No. 61/770,569, filed on Feb. 28, 2013.

(51) Int. Cl.
*A61M 5/00* (2006.01)
*A61M 37/00* (2006.01)

(52) U.S. Cl.
CPC ... *A61M 37/0015* (2013.01); *A61M 2037/003* (2013.01); *A61M 2037/0023* (2013.01);
(Continued)

(58) Field of Classification Search
CPC ...... A61M 37/0015; A61M 2037/0023; A61M 2037/0038; A61M 2037/003; A61M 2037/0007; A61K 9/0021
See application file for complete search history.

(56) References Cited

U.S. PATENT DOCUMENTS 3,964,482 A  6/1976  Gerstel et al.
5,250,023 A  10/1993 Lee et al.
(Continued)

FOREIGN PATENT DOCUMENTS

CN  201216811 Y  4/2009
EP  1682203        10/2003
(Continued)

OTHER PUBLICATIONS

PCT/IB2014/059344 Search Report and Written Opinion, dated Jun. 9, 2014. (18 pages).
(Continued)

*Primary Examiner* — Emily Schmidt
(74) *Attorney, Agent, or Firm* — Dority & Manning, P.A.

(57) ABSTRACT

A drug delivery device is disclosed that may include a skin penetrating assembly having a support defining an upper surface and a lower surface. The skin penetrating assembly may also include a plurality of skin penetrating members extending outwardly from the lower surface. Each skin penetrating member may define a channel for receiving a drug formulation. In addition, the device may include a reservoir positioned adjacent to the upper surface of the support for initially retaining the drug formulation. The reservoir may include a top surface and a bottom surface and may define a plurality of passages extending between the top and bottom surfaces. The passages may be configured such that the drug formulation is retained within the passages against gravity.

17 Claims, 7 Drawing Sheets

(52) U.S. Cl.
CPC ............... *A61M 2037/0038* (2013.01); *A61M 2037/0061* (2013.01); *A61M 2210/04* (2013.01)

(56) References Cited

U.S. PATENT DOCUMENTS

| | | | |
|---|---|---|---|
| 5,279,544 A | 1/1994 | Gross et al. | |
| 5,514,090 A | 5/1996 | Kriesel et al. | |
| 5,527,288 A | 6/1996 | Gross et al. | |
| 5,800,420 A | 9/1998 | Gross et al. | |
| 5,848,991 A | 12/1998 | Gross et al. | |
| 5,957,895 A | 9/1999 | Sage et al. | |
| 6,074,369 A | 6/2000 | Sage et al. | |
| 6,186,982 B1 | 2/2001 | Gross et al. | |
| 6,375,978 B1 | 4/2002 | Kleiner et al. | |
| 6,611,707 B1 | 8/2003 | Prausnitz et al. | |
| 6,623,457 B1 | 9/2003 | Rosenberg | |
| 6,656,147 B1 | 12/2003 | Gertsek et al. | |
| 6,780,171 B2 | 8/2004 | Gabel et al. | |
| 6,960,193 B2 | 11/2005 | Rosenberg | |
| 7,047,070 B2 | 5/2006 | Wilkinson et al. | |
| 7,115,108 B2 | 10/2006 | Wilkinson et al. | |
| 7,537,590 B2 | 5/2009 | Santini, Jr. et al. | |
| 7,611,481 B2 | 11/2009 | Cleary et al. | |
| 7,858,112 B2 | 12/2010 | Hatanaka et al. | |
| 7,896,837 B2 | 3/2011 | Wilkinson et al. | |
| 7,914,480 B2 | 3/2011 | Cleary et al. | |
| 8,029,469 B2 | 10/2011 | Ethelfeld | |
| 8,062,253 B2 | 11/2011 | Nielsen et al. | |
| 8,696,619 B2 | 4/2014 | Schnall | |
| 2002/0045859 A1* | 4/2002 | Gartstein | A45D 26/0004 604/117 |
| 2003/0014014 A1 | 1/2003 | Nitzan | |
| 2004/0106904 A1 | 6/2004 | Gonnelli et al. | |
| 2006/0036209 A1 | 2/2006 | Subramony et al. | |
| 2007/0224253 A1 | 9/2007 | Franklin | |
| 2007/0250018 A1 | 10/2007 | Adachi et al. | |
| 2008/0183144 A1 | 7/2008 | Trautman et al. | |
| 2009/0030365 A1 | 1/2009 | Tokumoto et al. | |
| 2009/0118672 A1 | 5/2009 | Gonnelli et al. | |
| 2010/0121307 A1 | 5/2010 | Lockard et al. | |
| 2010/0179473 A1 | 7/2010 | Genosar | |
| 2010/0209483 A1 | 8/2010 | Franklin | |
| 2011/0097393 A1 | 4/2011 | Al-Ghananeem | |
| 2011/0172601 A1 | 7/2011 | Beebe et al. | |
| 2011/0172609 A1 | 7/2011 | Moga et al. | |
| 2011/0172638 A1 | 7/2011 | Mora et al. | |
| 2011/0172645 A1 | 7/2011 | Moga et al. | |
| 2011/0264048 A1* | 10/2011 | O'Dea | A61M 37/0015 604/173 |
| 2011/0270221 A1* | 11/2011 | Ross | A61B 17/205 604/506 |
| 2012/0109065 A1 | 5/2012 | Backes | |
| 2012/0109067 A1 | 5/2012 | Ozawa et al. | |
| 2012/0245445 A1* | 9/2012 | Black | A61B 5/1468 600/365 |

FOREIGN PATENT DOCUMENTS

| | | | | |
|---|---|---|---|---|
| EP | 1471953 A2 | 11/2004 | | |
| WO | WO 03024508 A2 | 3/2003 | | |
| WO | WO 2005/039673 A2 | 5/2005 | | |
| WO | WO08007906 | 7/2007 | | |
| WO | WO2010062908 | 6/2010 | | |
| WO | WO 2010122222 A2 * | 10/2010 | ........... A61B 5/1411 |
| WO | WO2012168807 | 12/2012 | | |

OTHER PUBLICATIONS

Wisconsin/Tech Search Journal of Applied Physiology/ Measurement of Subcutaneous Tissue Fluid Pressure Using a Skin-Cup Method. Thomas H. Adair and Arthur C. Guyton May 1985. (11 pages).

Harcourt Publishers, Ltd. Model of Interstitial Pressure as a Result of Cyclical Changes in the Capillary Wall Fluid Transport S. Kurbel, B. Kurbel, T. Belovari, S. Maric, R. Steiner and D. Bozic. Medical Hypotheses (2001) 57(2), 161-166. (6 Pages).

* cited by examiner

DRUG DELIVERY DEVICE

CROSS REFERENCE TO RELATED APPLICATIONS

This application is a national phase application of International Patent Application No. PCT/IB2014/059344, filed on Feb. 28, 2014, which, in turn, is based upon and claims priority to U.S. Provisional Patent Application No. 61/770,569, filed on Feb. 28, 2013, both of which are hereby incorporated by reference herein in their entirety for all purposes.

FIELD OF THE INVENTION

The present subject matter relates generally to the delivery of drug formulations and, more particularly, to a passive drug delivery device.

BACKGROUND OF THE INVENTION

The delivery of drugs to a patient is conventionally performed in a variety of different ways. For example, intravenous delivery is by injection directly into a blood vessel; intraperitoneal delivery is by injection into the peritoneum; subcutaneous delivery is under the skin; intramuscular delivery is into a muscle; and oral delivery is through the mouth. One of the easiest methods for drug delivery, and for collection of body fluids, is through the skin. Skin is composed of the epidermis, including the stratum corneum, the stratum granulosum, the stratum spinosum, and the stratum basale, and the dermis, containing, among other things, the capillary layer. The stratum corneum is a tough, scaly layer made of dead cell tissue that extends around 10-20 microns from the skin surface and has no blood supply. Because of the density of this layer of cells, moving compounds across the skin, either into or out of the body, can be very difficult.

Current techniques for delivering local pharmaceuticals through the skin include methods that use needles or other skin piercing devices and methods that do not use such devices. Those methods that do not use needles typically involve: (a) topical applications, (b) iontophoresis, (c) electroporation, (d) laser perforation or alteration, (e) carriers or vehicles, which are compounds that modify the chemical properties of either the stratum corneum and/or the pharmaceutical, (f) physical pretreatment of the skin, such as abrasion of the stratum corneum (e.g., repeatedly applying and removing adhesive tape), and (g) sonophoresis, which involves modifying the barrier function of stratum corneum by ultrasound. Invasive procedures, such as use of needles or lances, can effectively overcome the barrier function of the stratum corneum. However, these methods suffer from several major disadvantages, including pain, local skin damage, bleeding, risk of infection at the injection site, and creation of contaminated needles or lances. These methods also usually require a trained administrator and are not suitable for repeated, long-term, or controlled use. Additionally, drug delivery through the skin has been relatively imprecise in both location and dosage of the pharmaceutical. Some of the problems include movement of the patient during administration, delivery of incomplete dosages, difficulties in administering more than one pharmaceutical at the same time, and difficulties in delivering a pharmaceutical to the appropriate part of the skin. Drugs have traditionally been diluted to enable handling of the proper dosages. This dilution step can cause storage as well as delivery problems.

Thus, it would be advantageous to be able to use small, precise volumes of pharmaceuticals for quick, as well as long-term, delivery into and/or through the skin.

Microneedles have been proposed for this purpose. The microneedles typically have a hollow shaft, similar to larger conventional medical needles, so that drug formulations may be delivered through the hollow shaft. Various mechanisms have been employed to initiate the flow of the drug formulation through such devices. U.S. Pat. No. 6,611,707 to Prausnitz et al. and U.S. Pat. No. 5,527,288 to Gross et al., for example, describe devices that each include a drug reservoir positioned over a housing that includes an array of hollow microneedles. A drug formulation is delivered from the reservoir by applying a force against the drug itself or against the reservoir, such as by pressing against the top of a flexible reservoir bag, to cause the formulation to flow out through the microneedles. Unfortunately, the flow rate of the drug formulation injected into the skin using such force is often far greater than the absorption rate of the skin itself. As a result, all or a significant portion of the drug formulation will often flow upwards at the interface between the skin and the microneedles to the surface of the skin.

As such, a need currently exists for a drug delivery system that can effectively deliver a drug formulation in a manner to improve the controlled delivery and bioavailability of the drug.

BRIEF DESCRIPTION OF THE INVENTION

Aspects and advantages of the invention will be set forth in part in the following description, or may be obvious from the description, or may be learned through practice of the invention.

In one aspect, the present subject matter is directed to a drug delivery device. The device may generally include a skin penetrating assembly having a support defining an upper surface and a lower surface. The skin penetrating assembly may also include a plurality of skin penetrating members extending outwardly from the lower surface. Each skin penetrating member may define a channel for receiving a drug formulation. In addition, the device may include a reservoir positioned adjacent to the upper surface of the support for initially retaining the drug formulation. The reservoir may include a top surface and a bottom surface and may define a plurality of passages extending between the top and bottom surfaces. The passages may be configured such that the drug formulation is retained within the passages against gravity.

In another aspect, the present subject matter is directed to a method for delivering a drug formulation. The method may include positioning a drug delivery device adjacent to skin, wherein the drug delivery device comprises a skin penetrating assembly including a support and a plurality of skin penetrating members extending outwardly from the support. The drug delivery device may also include a reservoir for initially retaining the drug formulation. The reservoir may define a plurality of passages. In addition, the method may include inserting the skin penetrating members into the skin such that a negative pressure is generated within the skin penetrating assembly due to skin absorption, wherein the passages are configured such that the drug formulation is retained within the passages against gravity until the negative pressure draws the drug formulation out of the passages and into the skin penetrating assembly.

These and other features, aspects and advantages of the present invention will become better understood with reference to the following description and appended claims. The accompanying drawings, which are incorporated in and constitute a part of this specification, illustrate embodiments of the invention and, together with the description, serve to explain the principles of the invention.

BRIEF DESCRIPTION OF THE DRAWINGS

A full and enabling disclosure of the present invention directed to one of ordinary skill in the art, is set forth in the specification, which makes reference to the appended figures, in which.

DETAILED DESCRIPTION OF THE INVENTION

Figure 1:
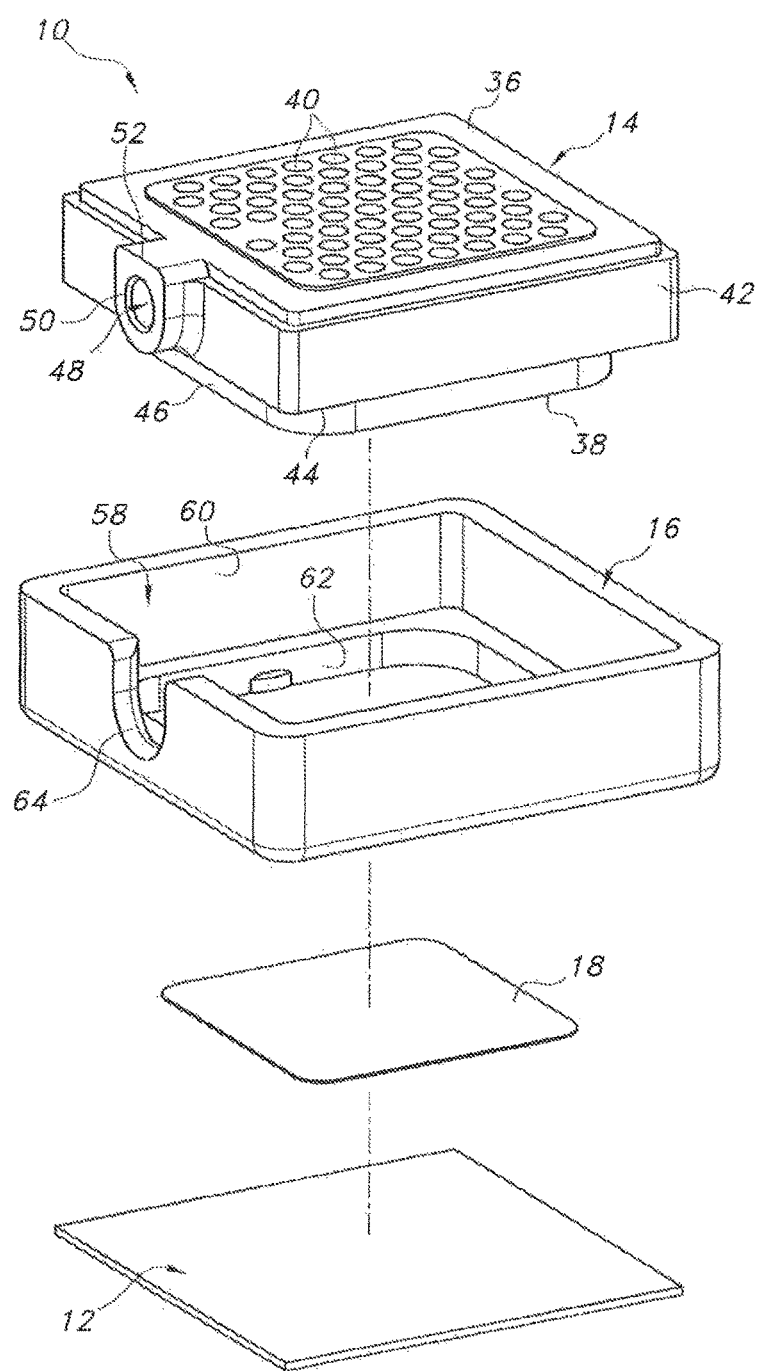
FIG. 1 illustrates an exploded, perspective view of various components that may be included within one embodiment of a drug delivery device in accordance with aspects of the present subject matter.
Figure 2:
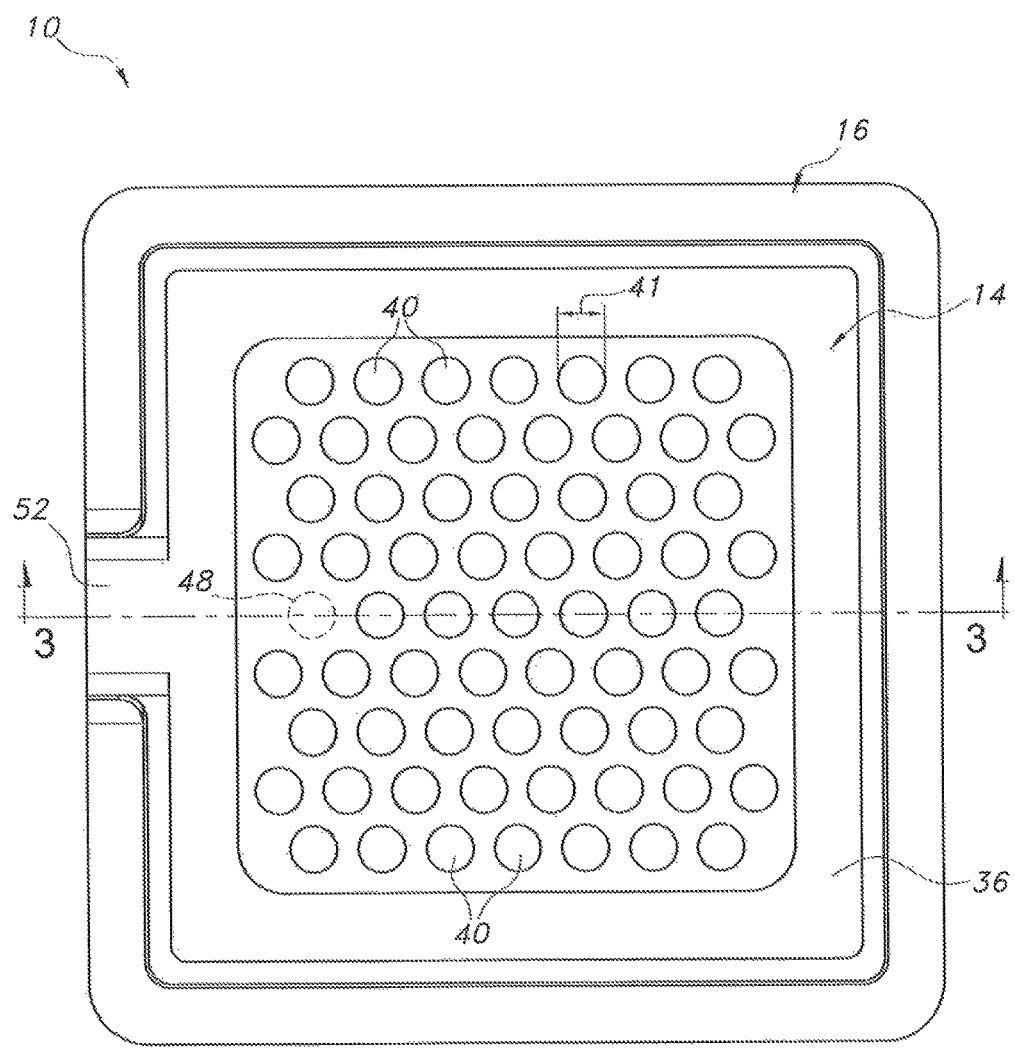
FIG. 2 illustrates a top, assembled view of the device components shown in FIG. 1.

Reference now will be made in detail to embodiments of the invention, one or more examples of which are illustrated in the drawings. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment can be used with another embodiment to yield a still further embodiment. Thus, it is intended that the present invention covers such modifications and variations as come within the scope of the appended claims and their equivalents.

In general, the present subject matter is directed to a drug delivery device configured to deliver a drug formulation into and/or through the skin of a user of the device. The device may generally include a skin penetrating assembly having a plurality of skin penetrating members (e.g., microneedles) and a reservoir configured to retain the drug formulation. In several embodiments, the drug formulation may be initially retained within a plurality of passages defined in the reservoir. Specifically, the dimensions of the passages and/or the material used to form the reservoir may be selected such that the drug formulation is retained within the passages against gravity (due to capillary action) until a negative pressure within the skin penetrating assembly, generated as a result of skin absorption, is sufficient to draw the drug formulation out of the passages and into the skin penetrating members for subsequent delivery into and/or through the user's skin. Accordingly, the flow of the drug formulation into and through the sin penetrating members may be driven entirely by skin absorption, thereby allowing the flow rate of the drug formulation through the device to generally match the absorption rate of the user's skin.

It should be appreciated that, in several embodiments of the present subject matter, the disclosed drug delivery device may be configured as a transdermal drug delivery device and, thus, may be designed to deliver a drug formulation(s) into but not through a user's skin (i.e., to a location between the stratum corneum and the inner surface of the epidermis). However, in other embodiments, the drug delivery device may be configured to deliver a drug formulation completely through the user's skin.

Referring now to the drawings, FIGS. 1-4 illustrate several views of various components that may form all or part of one embodiment of a drug delivery device 10 in accordance with aspects of the present subject matter. As shown, the device 10 may include a skin penetrating assembly 12 for delivering a fluidic drug formulation into and/or through the skin of a user of the device 10, a reservoir 14 for initially retaining the drug formulation, a reservoir frame 16 configured to receive and/or support at least a portion of the reservoir 14 and a spreading membrane 18 configured to be positioned between the skin penetrating assembly 12 and the reservoir 14.

In general, it should be appreciated that any suitable drug formulation(s) may be retained within and delivered via the disclosed device 10. As used herein, the term "drug formulation" is used in its broadest sense and may include, but is not limited to, any drug (e.g., a drug in neat form) and/or any solution, emulsion, suspension and/or the like containing a drug(s). Similarly, the term "drug" is used in its broadest sense and includes any compound having or perceived to have a medicinal benefit, which may include both regulated and unregulated compounds. For example, suitable types of drugs may include, but are not limited to, biologics, small molecule agents, vaccines, proteinaceous compounds, anti-infection agents, hormones, compounds regulating cardiac action or blood flow, pain control agents and so forth. One of ordinary skill in the art should readily appreciate that various ingredients may be combined together in any suitable manner so as to produce a compound having or perceived to have a medicinal benefit.

Referring generally to FIGS. 1-4, the skin penetrating assembly 12 may correspond to any suitable apparatus having any number of skin penetrating members (e.g., needles, microneedles and/or the like) that are capable of penetrating any portion of a user's skin, thereby allowing for the delivery of a drug formulation into and/or through the skin. For example, as described herein, the skin penetrating assembly 12 is configured as a microneedle assembly 12 having a plurality of microneedles 26. However, it should be appreciated that the present subject matter need not be limited to use with microneedle assemblies, but, rather, may be utilized with any suitable skin penetrating assembly have any suitable type of skin penetrating members.

Figure 4:
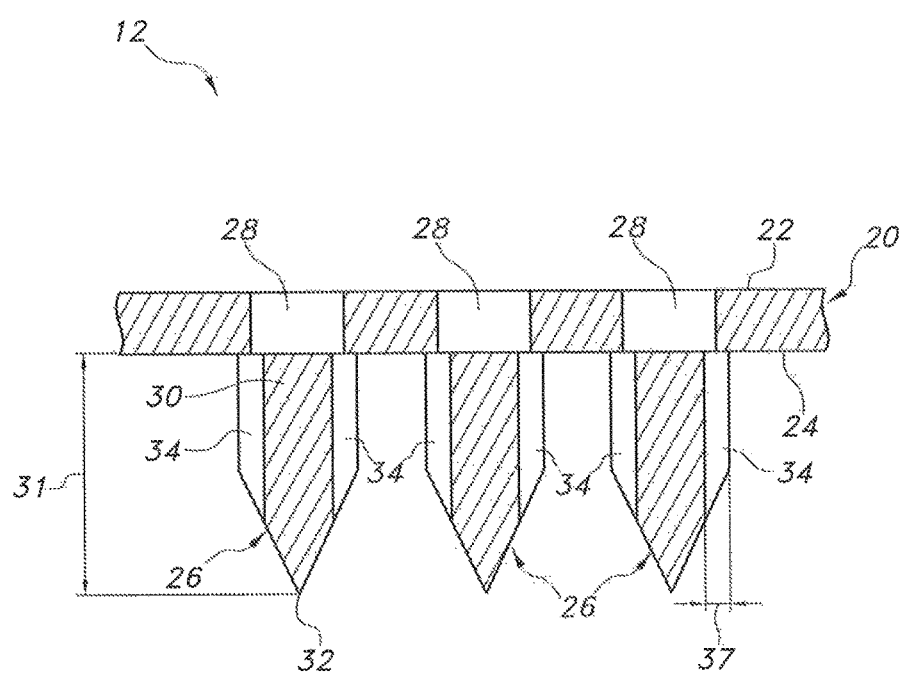
FIG. 4 illustrates a close-up view of a portion of a microneedle assembly of the device shown in FIG. 1.
Figure 5:
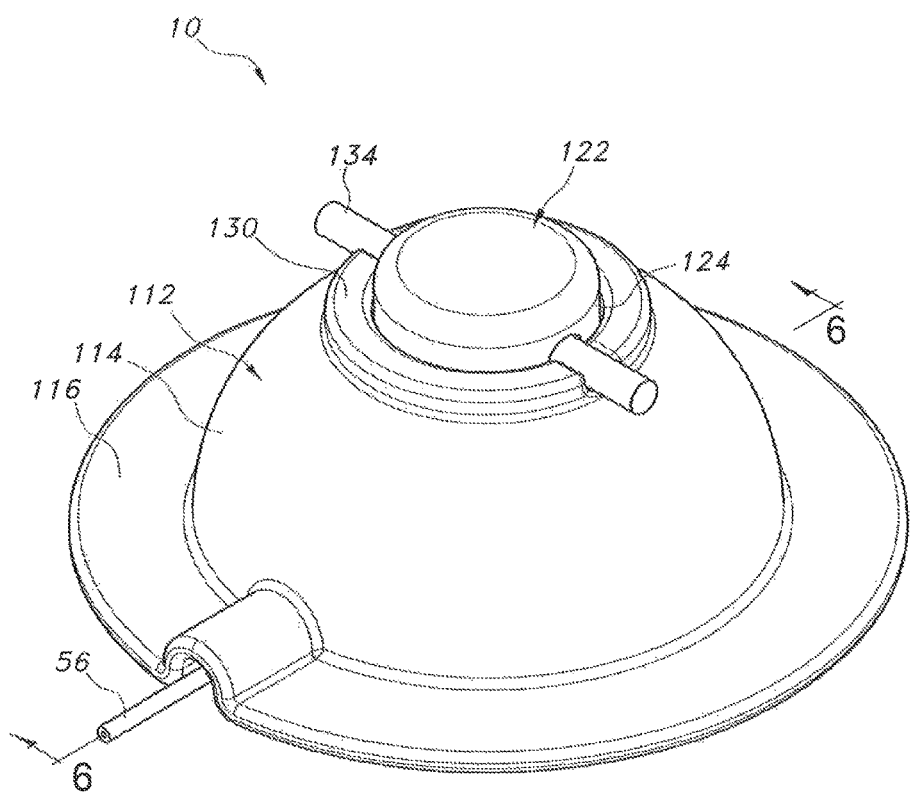
FIG. 5 illustrates a perspective, assembled view of various components that may be included within another embodiment of a drug delivery device in accordance with aspects of the present subject matter.

In general, the microneedle assembly 12 of the device 10 may have any suitable configuration known in the art for delivering a drug formulation into and/or through a user's skin. In several embodiments, the microneedle assembly 12 may include a plurality of skin penetrating members (i.e., microneedles) extending outwardly from a suitable substrate or support. For example, as shown in FIG. 4, the microneedle assembly 12 may include a support 20 defining a top surface 22 and a bottom surface 24 and a plurality of microneedles 26 extending outwardly from the bottom surface 24. The support 20 may generally be constructed from a rigid, semi-rigid or flexible sheet of material, such as a metal material, a ceramic material, a plastic material and/or any other suitable material. In addition, the support 20 may define one or more apertures between its top and bottom surfaces 22, 24 to permit the drug formulation to flow therebetween. For example, as shown in FIG. 4, a single aperture 28 may be defined in the support 20 at the location of each microneedle 26 to permit the drug formulation to be delivered from the top surface 22 to such microneedle 26. However, in other embodiments, the support 20 may define any other suitable number of apertures 28 positioned at and/or spaced apart from the location of each microneedle 26.

As shown in FIG. 4, each microneedle 26 of the microneedle assembly 12 may generally be configured to define a piercing or needle-like shape (e.g., a conical or pyramidal shape or a cylindrical shape transitioning to a conical or pyramidal shape) extending between a base 30 positioned adjacent to and/or extending from the bottom surface 24 of the support 20 and a tip 32 disposed opposite the base 30. As is generally understood, the tip 32 may correspond to the point of each microneedle 26 that is disposed furthest away from the support 20 and may define the smallest dimension of each microneedle 26. Additionally, each microneedle 26 may generally define any suitable length 31 between its base 30 and its tip 32 that is sufficient to allow the microneedles to penetrate the stratum corneum and pass into and/or through the epidermis. For example, in one embodiment, each microneedle 26 may define a length 31 of less than about 2000 micrometers (urn), such as less than about 1750 um, or less than about 1500 um, or less than about 1250 um and any other subranges therebetween. However, in certain embodiments, it may be desirable to limit the length 31 of the microneedles 26 such that they do not penetrate through the inner surface of the epidermis and into the dermis; such embodiments advantageously help minimize pain for the patient receiving the drug formulation. For example, in one embodiment, each microneedle 26 may define a length 31 of less than about 1000 micrometers (urn), such as a length ranging from about 900 um to about 100 um or from about 700 um to about 150 um or from about 500 um to about 175 um or from about 400 um to about 200 um and any other subranges therebetween. In a particular embodiment, the length 31 may range from about 25 um to about 1000 um, such as from about 100 um to about 1000 um or from about 200 um to about 1000 um and any other subranges therebetween.

It should also be appreciated that the length of the microneedles 26 may vary depending on the location at which the disclosed device 10 is being used on a user. For example, the length of the microneedles 26 for a device 10 to be used on a user's leg may differ substantially from the length of the microneedles 26 for a device 10 to be used on a user's arm.

Moreover, each microneedle 26 may define one or more channels 34 in fluid communication with the apertures 28 defined the support 20. In general, the channel(s) 34 may be defined at any suitable location on and/or within each microneedle 26. For example, as shown in FIG. 4, in one embodiment, the channel(s) 34 may be defined along an exterior surface of each microneedle 26. In another embodiment, the channels 34 may be defined through the interior of the microneedles 26 such that each microneedle 26 forms a hollow shaft. Regardless, the channels 34 may generally be configured to form a pathway that enables the drug formulation to flow from the top surface 22 of the support 20, through the apertures 28 and into the channels 34, at which point the drug formulation may be delivered into and/or through the user's skin.

It should be appreciated that the channels 34 may be configured to define any suitable cross-sectional shape. For example, in one embodiment, each channel 34 may define a semi-circular or circular shape. In another embodiment, each channel 34 may define a non-circular shape, such as a "v" shape or any other suitable cross-sectional shape.

In several embodiments, the dimensions of the channels 34 defined by the microneedles 26 and/or the apertures 28 defined in the support 20 may be specifically selected to induce a capillary flow of bodily fluid up through the microneedle assembly 12 when the microneedles 26 are initially inserted into the user's skin. As will be described below, such a capillary flow of bodily fluid upwards through the channels 34 and apertures 28 may generally force all of the air out of the microneedle assembly 12, thereby allowing for a continuous fluid path to be formed between the reservoir 14 and the microneedle assembly 12. Thereafter, as the user's skin begins to naturally reabsorb the bodily fluid, a negative pressure may be generated within the microneedle assembly 12 that draws and/or aids with the drawing of the drug formulation out of the reservoir 14 and into the microneedles 26 for subsequent delivery beneath the stratum corneum layer of the skin. It should be appreciated that, when delivering the drug formulation out of the reservoir 14 and through the microneedles 26, it may be desirable for the user's skin to provide a seal around the outer perimeter of the microneedles 26 in order to maintain the negative pressure at the interface between the microneedles 26 and the skin.

As is generally understood, capillary flow occurs when the adhesive forces of a fluid to the walls of a channel are greater than the cohesive forces between the liquid molecules. Additionally, the capillary pressure within a channel is inversely proportional to the cross-sectional dimension of the channel and directly proportional to the surface energy of the subject fluid, multiplied by the cosine of the static contact angle of the fluid at the interface defined between the fluid and the channel. Thus, the cross-sectional dimension 37 (FIG. 4) of the channel(s) 34 of each microneedle 26 (e.g., the diameter, width, etc.) may be carefully selected to facilitate capillary flow of the user's bodily fluid into the channels 34, with smaller dimensions generally resulting in higher capillary pressures. For example, in several embodiments, the cross-sectional area of each channel 34 may range from about 1,000 square microns ($um^2$) to about 125,000 $um^2$, such as from about 1,250 $um^2$ to about 60,000 $um^2$ or from about 6,000 $um^2$ to about 20,000 $um^2$ and any other subranges therebetween.

Moreover, as indicated above, the capillary pressure within the channels 34 may also be affected by the static contact angle of the fluid (i.e., the static state or equilibrium contact angle of the fluid), which is generally determined by the surface energy of the channel material and the surface tension of the fluid. As is generally understood, the static contact angle is defined between each channel 34 and the fluid contained therein. In several embodiments, the material used to form the microneedles 26 may be carefully selected such that the static contact angle is generally less than about 90 degrees, such as an angle ranging from less than 90 degrees to zero degrees or from about 60 degrees to about 5 degrees or from about 30 degrees to about 5 degrees and any other subranges therebetween. Suitable materials for the microneedles 26 may include, for example, silicon, thermoplastics and/or the like. It should also be appreciated that the surface of the microneedles 26 may be modified using any suitable surface treatment known in the art (e.g., a plasma surface treatment) to adjust the surface energy of the microneedles 26, thereby potentially modifying the contact angle defined between the channels 34 and the fluid.

As is generally understood, the body has a fluid pressure of about −300 pascals (Pa). Thus, in several embodiments, the dimensions of the channels 34 defined by microneedles 26 and/or the material used to form the microneedles 26 may be selected such that the capillary pressure within the channels 34 is larger (i.e., more negative) than −300 Pa, thereby allowing bodily fluid to be pulled out of the body and into the channels 34 upon insertion of the microneedles 26. For example, in a particular embodiment of the present subject matter, the capillary pressure within the channels 34 may range from about −4000 Pa to about −300 Pa, such as from about −1500 Pa to about −300 Pa or from about −1000 Pa to about −500 Pa and any other subranges therebetween. However, in other embodiments, the capillary pressure within the channels 34 may simply be less than zero Pa, such as a pressure ranging from about than about −4000 Pa to about −100 Pa. It should be appreciated that pressure values referred to herein may generally correspond to time-weighted average pressures.

It should also be appreciated that FIG. 4 only illustrates a portion of a suitable microneedle assembly 12 and, thus, the microneedle assembly 12 may generally include any number of microneedles 26 extending from its support 20. For example, in one embodiment, the actual number of microneedles 26 included within the microneedle assembly 12 may range from about 10 microneedles per square centimeter ($cm^2$) to about 1,500 microneedles per $cm^2$, such as from about 50 microneedles per $cm^2$, to about 1250 microneedles per $cm^2$ or from about 100 microneedles per $cm^2$ to about 500 microneedles per $cm^2$ and any other subranges therebetween.

Additionally it should be appreciated that the microneedles 26 may generally be arranged on the support 20 in a variety of different patterns, and such patterns may be designed for any particular use. For example, in one embodiment, the microneedles 26 may be spaced apart in a uniform manner, such as in a rectangular or square grid or in concentric circles. In such an embodiment, the spacing of the microneedles 26 may generally depend on numerous factors, including, but not limited to, the length and width of the microneedles 26, as well as the amount and type of drug formulation that is intended to be delivered through the microneedles 26.

Figure 3:
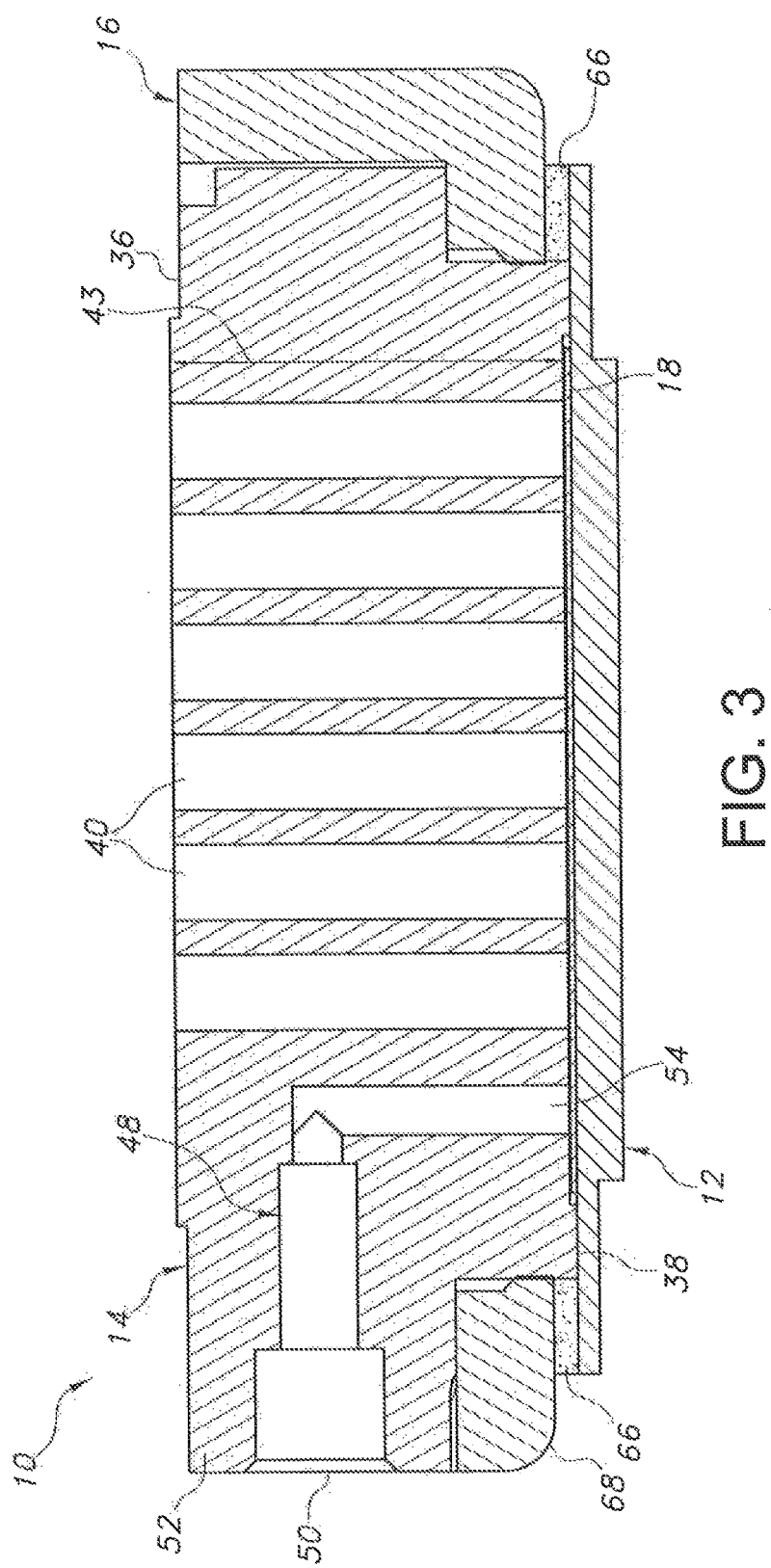
FIG. 3 illustrates a cross-sectional view of the device components shown in FIG. 2 taken about line 3-3.

Referring still to FIGS. 1-4, the reservoir 14 of the disclosed device 10 may generally be configured as a solid block or body defining a plurality of capillaries or passages for initially retaining the drug formulation prior to the subsequent delivery of the formulation into the microneedle assembly 12. Specifically, as shown in FIGS. 1 and 3, the reservoir 14 may include a top surface 36 and a bottom surface 38 and may define a plurality of passages 40 extending between the top and bottom surfaces 36, 38. The body of the reservoir 14, itself, may generally define any suitable shape and/or may have any suitable configuration that the permits the reservoir 14 to function as described herein. For example, as shown in FIG. 1, in one embodiment, the reservoir body may include an upper portion 42 defining a generally rectangular shape that extends from the top surface 36 to a central peripheral edge 44 of the reservoir 14 and a lower portion 46 defining a generally rectangular shape that extends from the peripheral edge 44 to the bottom surface 38, with the lower portion 46 being recessed relative to upper portion 42. However, in other embodiments, the body of the reservoir 14 may have any other suitable configuration and/or define any other suitable shape.

It should be appreciated that the passages 40 may generally have any suitable orientation within the reservoir 14 between its top and bottom surfaces 36, 38. However, in several embodiments, the passages 40 may be oriented within the reservoir such that each passage 40 extends substantially perpendicular to the microneedle assembly 12 and/or substantially parallel to the lengthwise direction of each microneedle 26.

The passages 40 defined through the reservoir 14 may generally be configured such that the drug formulation is retained within the reservoir 14 against gravity until it is drawn out passively due to skin absorption. Specifically, in several embodiments, the dimensions of each passage 30 may be selected to permit the drug formulation to be retained within the passages 40 due to capillary action until a negative pressure is generated within the microneedle assembly 12 that is sufficient to draw the drug formulation out of the passages 40 and into the microneedles 26. As indicated above, capillary flow occurs when the adhesive forces of a fluid to the walls of a channel are greater than the cohesive forces between the liquid molecules, with greater capillary pressures being achieved with smaller cross-sectional dimensions. Thus, the cross-sectional dimension 41 (FIG. 2) of each passage 40 (e.g., diameter, width, etc.) may be carefully selected such that a capillary pressure is generated within each passage 40 that is sufficient to initially retain the drug formulation within the passages 40. For example, in several embodiments, the cross-sectional area of each passage 40 may range from about 1,000 square microns ($um^2$) to about 125,000 $um^2$, such as from about 1,250 $um^2$ to about 60,000 $um^2$ or from about 6,000 $um^2$ to about 20,000 $um^2$ and any other subranges therebetween.

Moreover, the capillary pressure required to hold the drug formulation against gravity may also vary as a function of the height 43 (FIG. 3) of the passages 40. Thus, in several embodiments, the height 43 of each passage 40 may also be carefully selected to ensure that the drug formulation is initially retained within the passages 40. For example, in a particular embodiment, the height 43 of each passage 40 may be less than about 3 centimeters (cm), such as a height ranging from about 1.5 cm to about 0.5 cm or from about 1 cm to about 0.5 cm and any other subranges therebetween.

It should be appreciated that the particular number of passages 40 formed in the reservoir 14 may generally vary depending on numerous factors, including, but not limited to, the cross-sectional dimension 41 of each of the passages 40 and the total volume of the drug formulation desired to be retained within the reservoir 14. However, in a particular embodiment of the present subject matter, the number of passages 40 formed in the reservoir 14 may range from about 10 passages per square centimeter ($cm^2$) to about 1,500 passages per $cm^2$, such as from about 50 passages per $cm^2$, to about 1250 passages per $cm^2$ or from about 100 passages per $cm^2$ to about 500 passages per $cm^2$ and any other subranges therebetween. It should also be appreciated that the passages 40 may be configured to define any suitable cross-sectional shape. For example, in one embodiment, each passage 40 may define a semi-circular or circular shape. In another embodiment, each passage 40 may define a non-circular shape, such as a diamond cross-sectional shape or any other suitable cross-sectional shape.

Additionally, as indicated above, the capillary pressure within the passages 40 may also be affected by the contact angle, which is generally determined by the surface energy of the passage material and the surface tension of the drug formulation. As such, the material used to form the reservoir body itself may be carefully selected to further enhance the drug delivering capabilities of the disclosed device 10. Specifically, it may be desirable for the selected material to have a sufficient affinity for the drug formulation to allow it to be initially retained within the passages 40 while still allowing the drug formulation to be passively drawn out of the passages 40 by the negative pressure generated within the microneedle assembly 12 due to skin absorption. In several embodiments, the material used to form the reservoir 14 may be selected such that a static contact angle is defined between the drug formulation and the passages 40 that is less than about 90 degrees, such as an angle ranging from less than 90 degrees to zero degrees or from about 60 degrees to about 5 degrees or from about 30 degrees to about 5 degrees and any other subranges therebetween. In considering these ranges, it has been found that certain nylon materials (e.g., nylon 6), poly-acrylic materials, silicon materials, glass materials and thermoplastic materials may provide such desired characteristics. However, it should be appreciated that the reservoir 14 may generally be formed from any suitable material that permits it to function as described herein.

It should be appreciated that the capillary pressure within the passages 40 may generally be smaller (i.e., less negative or closer to a zero pressure) than the capillary pressure within the channels 34 of the microneedles 26. However, as indicated above, it is desirable for the capillary forces within the passages 40 to be sufficient to initially retain the drug formulation within the passages 40 against gravity. Thus, in several embodiments, the capillary pressure within each passage 40 may generally be large enough to generate a capillary force that is greater than the gravitational force acting on the drug formulation (preferably greater than two times the gravitational force).

It should also be appreciated that the drug formulation may be supplied to the reservoir 14 in a variety of different ways. For example, in several embodiments, the drug formulation may be supplied to reservoir 14 via an inlet channel 48 defined through a portion of the reservoir body. For example, as shown in FIGS. 1 and 3, in one embodiment, an inlet channel 48 may formed within the reservoir 14 that extends between an inlet 50 defined through a projection 52 extending outwardly from the upper portion 42 of the reservoir 14 and an outlet 54 defined through the bottom surface 38 of the reservoir 14. In such an embodiment, a suitable conduit or tube 56 (FIG. 8) may be configured to be received within the inlet 50 and may be in fluid communication with a suitable drug source (e.g., a syringe containing the drug formulation) such that the drug formulation may be directed into the inlet channel 48 and expelled from the outlet 54 along the bottom surface 38 of the reservoir 14. The drug formulation may then be drawn upwards into the passages 40 via capillary action.

However, in others embodiments, the drug formulation may be supplied to the reservoir 14 using any other suitable method. For example, in another embodiment, the lower portion 46 of the reservoir 14 may simply be placed in fluid communication with the drug formulation (e.g., by dipping the reservoir 14 into a container holding the drug formulation) to allow the formulation to flow upward into the passages 40 via capillary action.

Referring still to FIGS. 1-4, the reservoir frame 16 may generally be configured as a rigid or semi-rigid body defining a frame opening 58 configured to receive at least a portion of the reservoir 14, thereby allowing the reservoir 14 to be supported within the frame 65. Thus, it should be appreciated that, in several embodiments, the frame opening 58 may generally be formed in the frame 16 so as to define a shape corresponding to the overall shape of the body of the reservoir 14. For example, as shown in FIG. 1, an upper portion 60 of the frame opening 58 may be configured to define a generally rectangular-shaped opening corresponding to the rectangular shape of the upper portion 42 of the reservoir 14. Similarly, a lower portion 62 of the frame opening 58 may be reduced in size so as to define an opening generally corresponding to shape of the recessed, lower portion 46 of the reservoir 14. Additionally, as shown in FIG. 1, the frame 16 may also define an inlet recess 64 configured receive the outwardly extending projection 52 of the reservoir 14. As such, when the reservoir 14 is received within the frame opening 58, the reservoir 14 may be vertically supported within the frame 16.

Additionally, in several embodiments, the reservoir frame 16 may be configured to be coupled to the microneedle assembly 12. For example, as shown in FIG. 3, a suitable adhesive 66 (e.g., a pressure sensitive adhesive) may be applied between a bottom surface 68 of the reservoir frame 16 and the periphery of the top surface of the microneedle assembly 12 (i.e., the top surface 22 of the support 20) to secure the microneedle assembly 12 to the reservoir frame 16. However, in other embodiments, the microneedle assembly 12 may be configured to be coupled to a portion of the reservoir 14 (e.g., along the outer periphery of the bottom surface 38 of the reservoir 14).

As indicated above, the device 10 may also include a spreading membrane 18 disposed between the microneedle assembly 12 and the reservoir 14. Specifically, as shown in FIG. 3, the spreading membrane 18 may be disposed at the interface defined between the top surface of the microneedle assembly 12 and the bottom surface 38 of the reservoir 14. In general, the spreading membrane 18 may be fabricated from any suitable permeable, semi-permeable or microporous material(s) (e.g., a nylon filter mesh) that allows for the flow and/or distribution of the drug formulation therethrough. For example, in one embodiment, the material used to form the spreading membrane 18 may have an average pore size of from about 0.01 micron to about 1000 microns, such as from about 1 micron to about 500 microns or from about 20 microns to about 200 microns and any other subranges therebetween. Additionally, in a particular embodiment, the material used to form the spreading membrane 18 may have an average pore size ranging from about 0.01 micron to about 1 micron, such as from about 0.1 micron to about 0.9 micron or from about 0.25 micron to about 0.75 micron and any other subranges therebetween. Regardless, the spreading membrane 18 may be configured to distribute the drug formulation evenly along the bottom surface 38 of the reservoir 14. For example, as shown in the illustrated embodiment, the drug formulation flowing through the inlet channel 48 may be expelled via the outlet 54 into the spreading membrane 18, which may then distribute the formulation along the bottom surface 38 of reservoir 38 so that it may be drawn upwards into the passages 40 via capillary action.

It should be appreciated that, in one embodiment, a slight gap may be defined between the spreading membrane 18 and the bottom surfaces of the passages 40 to assist in distributing the formulation along the bottom surface 38 of reservoir 38. It should also be appreciated that, in one embodiment, the drug formulation may be contained within the passages 40 prior to the microneedle assembly 12 being coupled to the reservoir frame 16.

Additionally, the spreading membrane 18 may also serve as a fluid interface between the reservoir 14 and the microneedle assembly 12. Specifically, as indicated above, when the microneedles 26 initially penetrate the user's skin, the channels 34 defined in the microneedles 26 and the apertures 28 defined in the microneedle support 20 may be configured such that bodily fluid is drawn into the microneedle assembly 12 via capillary action. Thus, as the bodily fluid flows upwards through the microneedle assembly 12, any air contained within channels 34 and/or apertures 28 may be forced upward and out of the microneedle assembly 12. Such evacuation of the air from the microneedle assembly 12 may generally allow for the creation a continuous fluid connection between the reservoir passages 40 and the microneedle assembly 12 as the bodily fluid contacts or otherwise flows upward into the spreading membrane 18. Thereafter, as the bodily fluid is naturally absorbed back into the skin, a negative pressure (e.g., −300 Pa) may be generated within the microneedle assembly 12 due to such skin absorption that is sufficient to overcome the capillary pressure retaining the drug formulation within the passages 40. As such, the drug formulation may be drawn out of the reservoir 14 and through the microneedles 26 at a flow rate that generally corresponds to the absorption rate of the skin.

Referring now to FIGS. 5-8, several views of additional components that may also form all or part of the disclosed drug delivery device 10 are illustrated in accordance with aspects of the present subject matter. As shown, in addition to the microneedle assembly 12, reservoir 14, reservoir frame 16 and spreading membrane 18, the device 10 may also include an outer housing 112 configured to at least partially surround and/or encase the various components of the device 10. For example, as particularly shown in FIGS. 5 and 8, the housing 112 may include an upper housing portion 114 defining an open volume for housing the various device components. The upper housing portion 112 may generally be configured to define any suitable shape. For instance, as shown in the illustrated embodiment, the upper housing portion 114 may define a semi-circular or dome shape. However, in other embodiments, the upper housing portion 114 may have any other suitable shape that defines an open volume for housing the various components of the device 10.

In addition, the housing 112 may include a lower housing portion 116 configured to be positioned adjacent to the user's skin when the device 10 is in use. As shown, the lower housing portion 116 may generally be configured as a flange or projection extending outwardly from the bottom periphery of the upper portion 114 of the housing 112. In several embodiments, the lower housing portion 116 may be configured to be attached to the user's skin using a skin attachment means. For example, in one embodiment, a suitable adhesive 118 may be applied to a bottom surface 120 of the lower housing portion 116. As such, when the lower housing portion 116 is placed onto the user's skin, the adhesive may secure the housing 112 to the skin.

Figure 6:
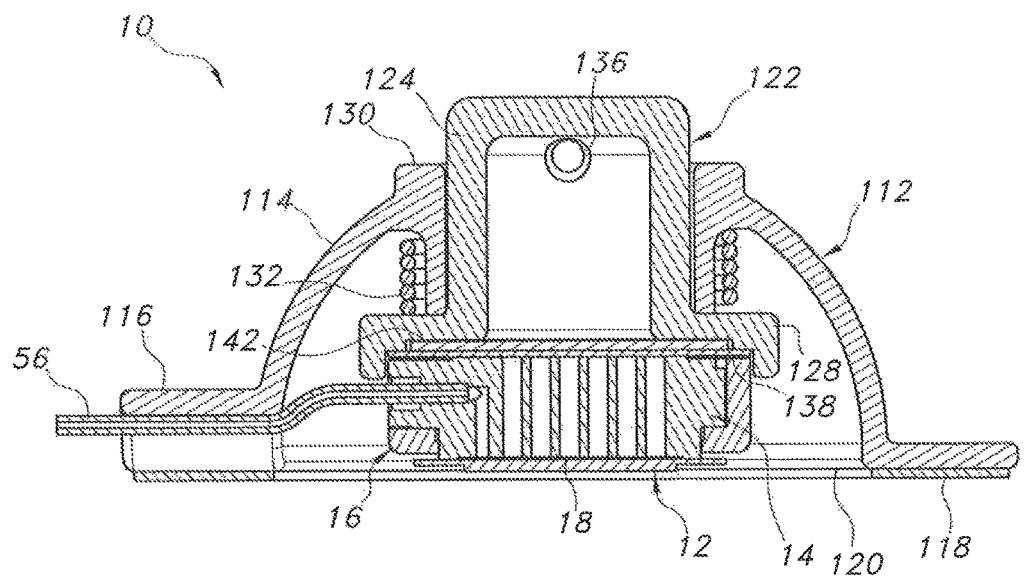
FIG. 6 illustrates a cross-sectional view of the device components shown in FIG. 5 taken about line 6-6, particularly illustrating a plunger of the device in an un-actuated position.
Figure 7:
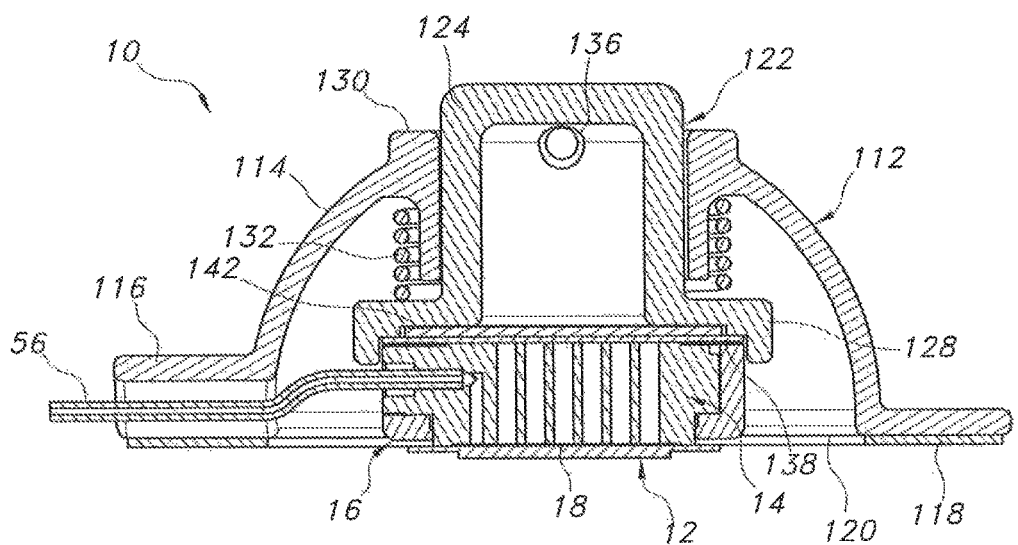
FIG. 7 illustrates another cross-sectional view of the device components shown in FIG. 5, particularly illustrating the plunger in an actuated position.
Figure 8:
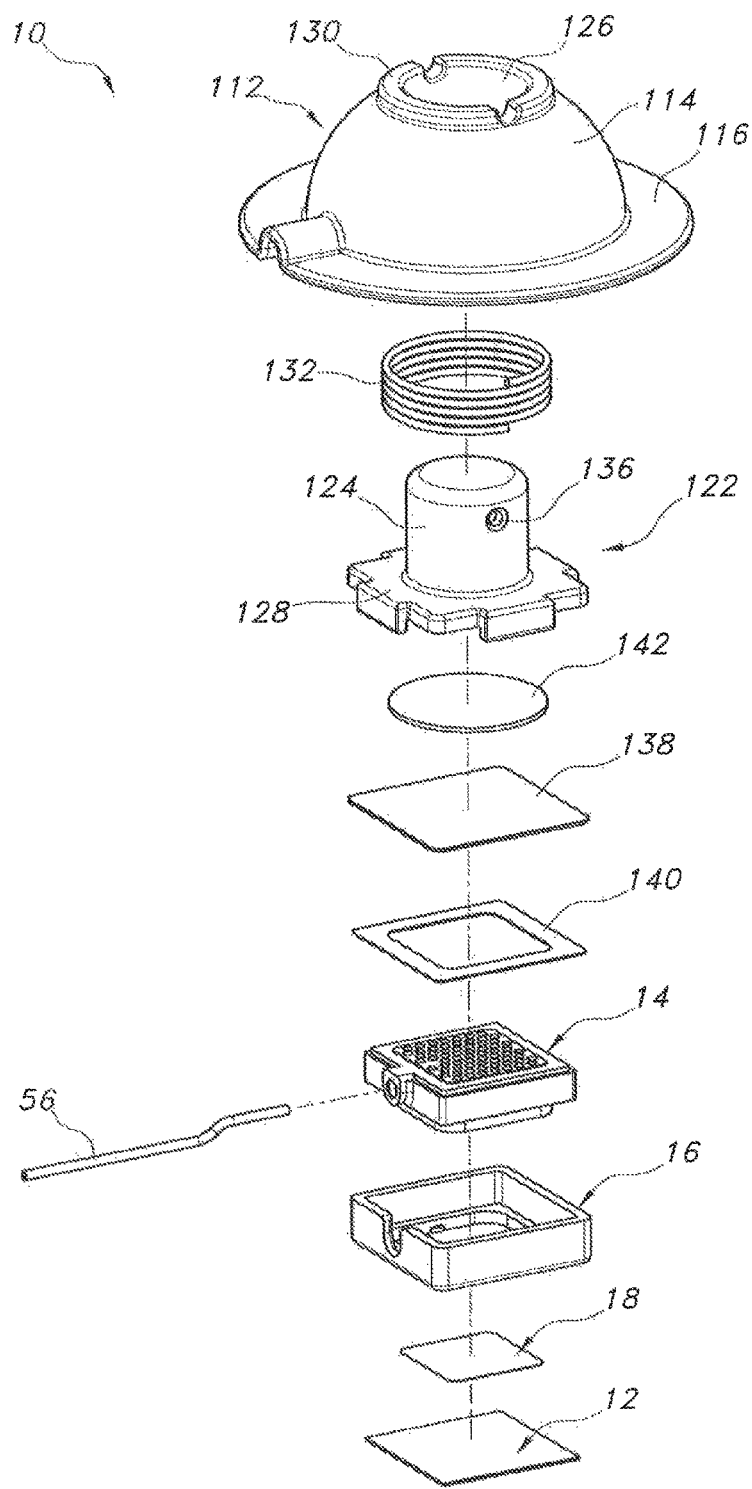
FIG. 8 illustrates an exploded perspective view of the device components shown in FIGS. 5-7.

Moreover, the device 10 may also include a plunger 122 configured to be moved relative to the housing 112 between un-actuated position (FIG. 6), wherein the bottom of the microneedle assembly 12 is generally aligned with or recessed relative to the bottom surface 120 of the lower housing portion 116 and an actuated position (FIG. 7), wherein the microneedle assembly 12 extends outward beyond the bottom surface 120 of the lower housing portion 116, thereby allowing the microneedles 26 of the microneedle assembly 12 to penetrate the user's skin. As shown in FIGS. 6-8, in one embodiment, the plunger 122 may generally include a cylindrical top portion 124 configured to be slidably received within a corresponding opening 126 defined in the housing 112 and a flattened bottom portion 128 configured to engage or otherwise apply a force against the reservoir 14 and/or reservoir frame 16. In such an embodiment, when the top portion 124 of the plunger 122 is moved downward within the opening 126 relative to a top surface 130 of the housing 112, the bottom portion 128 of the plunger 122 may apply a force against the reservoir 14 and/or reservoir frame 16 that pushes the microneedle assembly 12 downward into the user's skin.

It should be appreciated that the plunger 122 may be configured to be pushed downward against the reservoir 14 and/or reservoir frame 16 using any suitable means known in the art. For example, as shown in the illustrated embodiment, a spring 132 may be positioned between the bottom portion 128 of the plunger 122 and the upper housing portion 114 of the housing 112 so as apply a downward force against the plunger 122. In such an embodiment, a lock pin and/or other locking mechanism may be configured to maintain the plunger 122 in the un-actuated position when the device 10 is not use. For example, as shown in FIG. 1, a lock pin 134 may be configured to extend through an opening 136 defined in the plunger 122 so as to engage opposing sides of the upper housing portion 114, thereby preventing the plunger 122 from moving relative to the housing 112. However, when the lock pin 134 is removed, the force applied by the spring 132 may push the plunger 122 downward into the actuated position, thereby causing the microneedle assembly 12 to be moved in the direction of the user's skin.

In one embodiment, the configuration of the spring 132 (including its length and spring constant) may be selected such that the downward force transmitted to the microneedle assembly 12 is sufficient to cause the microneedles 26 to penetrate the user's skin and remain therein during delivery of the drug formulation without any additional force applied to the plunger 122. Alternatively, the configuration of the spring 132 may be selected so that an additional downward force is required to cause the microneedles 26 to penetrate the user's skin and/or remain therein during delivery of the drug formulation. In such an embodiment, the additional downward force may be applied, for example, by the user pressing down against the top of the plunger 122.

It should be appreciated that, in addition to the downward force applied by the spring 132, a reactive, upward force may also be applied by the spring 132 against the housing 112. Due to the configuration of the disclosed device 10, such upward force may generally be transmitted through the housing 112 to the user's skin via the adhesive 118 used to secure the housing 112 to the user. As such, the user's skin may be tightened as it is pulled upward around the periphery of the housing 112, thereby enhancing the ease in which the microneedles 26 may be inserted into the skin.

It should also be appreciated that, in alternative embodiments, the plunger 122 may be moved relative to the housing 112 using any other suitable means known in the art. For example, in one embodiment, the user simply may apply finger pressure to the top of the plunger 122 to push it downward. Moreover, in other embodiments, the disclosed device 10 may include any other suitable means known in the art for generating and/or applying pressure to the microneedle assembly 12 and/or the reservoir 14. For instance, fluid pressure (e.g., pressurized air derived from reactions and/or pumped into the device 10) may be used to apply pressure to the microneedle assembly 12 and/or the reservoir 14. In another embodiment, any other suitable device and/or actuator (e.g., a turn/crank mechanism, a displacement cylinder and/or the like) may be used to apply a mechanical force against the microneedle assembly 12 and/or the reservoir 14.

Additionally, it should be noted that, since the reservoir 14 is designed such that the drug formulation is retained within the passages 40, the disclosed plunger 122 does not apply a significant force against the drug formulation itself. Rather, when a downward force is applied by the plunger 122, the force is transmitted through the body of the reservoir 14 and/or the reservoir frame 16. Accordingly, the microneedles 26 may be pressed into the user's skin without increasing the pressure of the drug formulation or otherwise pushing downward onto the drug formulation, thereby preventing the drug formulation from being forced through the microneedles 26 at an undesirable flow rate.

Referring still to FIGS. 5-8, the device 10 may also include a filter 138 configured to allow air (including any air rising upward from the microneedle assembly 12) to be vented from the reservoir 14. As shown FIGS. 6 and 7, the filter 138 may be configured to be positioned directly adjacent to the top surface 36 of the reservoir 14 so as to cover the top end of each passage 40. In such an embodiment, the filter 138 may be attached to the reservoir 14 around the periphery of its top surface 36. For example, as shown in FIGS. 6-8, a suitable adhesive 140 (e.g., a pressure sensitive adhesive) may be disposed between the filter 138 and the top surface 36 in order to secure the filter 138 to the reservoir 16.

In general, it should be appreciated that the filter 138 may be formed from any suitable air permeable material that at least partially resists and/or repels the passage of the drug formulation therethrough. In certain embodiments, it may be desirable for the filter 138 to readily allow the passage of air and to completely or substantially prevent the passage of fluids including any carriers or diluents such as alcohol or water. For example, in several embodiments, the filter 138 may be formed from a highly hydrophobic and oleophobic material(s), such as certain acrylic copolymer membranes, other hydrophobic polymer(s) and/or any other suitable material(s).

Additionally, as shown in FIG. 8, in several embodiments, a rigid or semi-rigid screen 142 (e.g., a metal wire mesh) may be positioned between the filter 138 and the plunger 122. Thus, as the plunger 122 is pushed downward against the screen 142 (e.g., via the force applied by the spring 132), the screen 142 may maintain the filter 138 flat against the top surface 36 of the reservoir 14 while permitting air to pass therethrough. As such, the filter 138 may completely cover/seal the top of each passage 40, thereby allowing the filter 138 to serve as a means for resisting or repelling the flow of the drug formulation along the top surface 36 of the reservoir 14.

It should be appreciated that, in various embodiments of the present subject matter, the disclosed device 10 may include all or any combination of the components shown in FIGS. 1-8. For instance, in one embodiment, the device 10 may simply comprise the microneedle assembly 12, the reservoir 14 and the spreading membrane 18 or any other suitable combination of the disclosed components.

It should also be appreciated that the present subject matter is also directed to a method for delivering a drug formulation. In several embodiments, the method may include positioning the drug delivery device 10 adjacent to the skin and inserting the microneedles 26 into the skin such that a negative pressure is generated within the microneedle assembly due to skin absorption that draws the drug formulation out of the passages 40 of the reservoir 14.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they include structural elements that do not differ from the literal language of the claims, or if they include equivalent structural elements with insubstantial differences from the literal languages of the claims.

What is claimed is:

1. A drug delivery device comprising:
a skin penetrating assembly including a support defining an upper surface and a lower surface, the support further defining a plurality of apertures extending between the upper and lower surfaces, the skin penetrating assembly further including a plurality of skin penetrating members extending outwardly from the lower surface, each skin penetrating member defining a channel for receiving a drug formulation, each channel being in fluid communication with at least one of the plurality of apertures; and
a separate reservoir positioned adjacent to the upper surface of the support that initially retains the drug formulation, the reservoir including a top surface and a bottom surface and defining a plurality of passages extending between the top and bottom surfaces, the passages being configured such that the drug formulation is retained within the passages against gravity prior to delivery of the drug formulation to the skin penetrating assembly,
wherein a cross-sectional area of each passage is selected such that a capillary pressure is generated within each passage that retains the drug formulation against gravity until a negative pressure is generated within the skin penetration assembly due to skin absorption that draws the drug formulation out of the passages and into the skin penetration assembly.

2. The drug delivery device of claim 1, wherein a cross-sectional area of each channel is selected such that bodily fluid flows upward into the skin penetration assembly via capillary action when the skin penetrating members are inserted into skin.

3. The drug delivery device of claim 1, wherein a capillary pressure within each channel ranges from about −4000 pascals to about −300 pascals.

4. The drug delivery device of claim 3, wherein the capillary pressure within each passage is less than the capillary pressure within each channel.

5. The drug delivery device of claim 1, wherein the skin penetrating assembly is configured as a microneedle assembly including a plurality of microneedles extending outwardly from the lower surface of the support.

6. The drug delivery device of claim 1, wherein a length of each skin penetrating member is less than about 1000 micrometers.

7. The drug delivery device of claim 1, further comprising a spreading membrane disposed between the upper surface of the skin penetrating assembly and the reservoir, the spreading membrane being configured to distribute the drug formulation along the bottom surface of the reservoir.

8. The drug delivery device of claim 1, further comprising a filter positioned adjacent to the top surface of the reservoir, the filter being configured to allow air to be vented from the reservoir.

9. The drug delivery device of claim 1, further comprising a reservoir frame defining a frame opening configured to receive at least a portion of the reservoir, the skin penetrating assembly being coupled to the reservoir frame.

10. A method for delivering a drug formulation, the method comprising:
   positioning a drug delivery device adjacent to skin, wherein the drug delivery device comprises:
   a skin penetrating assembly including a support and a plurality of skin penetrating members extending outwardly from the support, the support defining a plurality of apertures therein, each skin penetrating member defining a channel for receiving the drug formulation, each channel being in fluid communication with at least one of the plurality of apertures; and
   a separate reservoir initially retaining the drug formulation, the reservoir defining a plurality of passages; and
   inserting the skin penetrating members into the skin such that a negative pressure is generated within the skin penetrating assembly due to skin absorption, wherein a cross-sectional area of each passage is selected such that a capillary pressure is generated within each passage that retains the drug formulation within the passages against gravity until the negative pressure draws the drug formulation out of the passages and into the skin penetrating assembly.

11. The method of claim 10, wherein a cross-sectional area of each channel is selected such that bodily fluid flows upward into the skin penetration assembly via capillary action when the skin penetrating members are inserted into skin.

12. The method of claim 10, wherein a capillary pressure within each channel ranges from about −4000 pascals to about −300 pascals.

13. The method of claim 12, wherein the capillary pressure within each passage is less than the capillary pressure within each channel.

14. The method of claim 10, wherein the skin penetrating assembly is configured as a microneedle assembly including a plurality of microneedles extending outwardly from the lower surface of the support.

15. The method of claim 10, wherein a length of each skin penetrating member is less than about 1000 micrometers.

16. The method of claim 10, further comprising a spreading membrane disposed between the skin penetrating assembly and the reservoir, the spreading membrane being configured to distribute the drug formulation along the bottom surface of the reservoir.

17. The method of claim 10, further comprising a filter positioned adjacent to the top surface of the reservoir, the filter being configured to allow air to be vented from the reservoir.

* * * * *